United States Patent [19]

Heeb et al.

[11] 4,243,548

[45] Jan. 6, 1981

[54] PRESSURIZED AEROSOL FORMULATION AND PROCESS FOR THE MANUFACTURE THEREOF

[75] Inventors: Dieter Heeb; Uwe Bergemann; Claus-Dieter Frenzel, all of Hamburg, Fed. Rep. of Germany

[73] Assignee: Hans Schwarzkopf GmbH, Hamburg, Fed. Rep. of Germany

[21] Appl. No.: 964,010

[22] Filed: Nov. 27, 1978

[30] Foreign Application Priority Data

Nov. 25, 1977 [CH] Switzerland ................. 14492/77

[51] Int. Cl.$^3$ .................. C09K 3/30; B65B 7/00; B65B 31/10
[52] U.S. Cl. ............................ 252/305; 53/470; 252/364; 252/522 R; 424/45; 424/47; 424/DIG. 1; 424/DIG. 2
[58] Field of Search ............... 252/305; 424/45, 47

[56] References Cited

U.S. PATENT DOCUMENTS

| | | | |
|---|---|---|---|
| 2,964,165 | 12/1960 | Riley | 252/305 X |
| 3,131,154 | 4/1964 | Klausner | 252/305 |
| 3,207,386 | 9/1965 | Presant et al. | 252/305 X |
| 3,387,425 | 6/1968 | Flanner | 252/305 X |
| 3,996,153 | 12/1976 | Heeb et al. | 252/305 |
| 4,134,968 | 1/1979 | Stebles | 424/47 |

*Primary Examiner*—Richard D. Lovering
*Attorney, Agent, or Firm*—Beveridge, DeGrandi, Kline and Lunsford

[57] ABSTRACT

The subject of the invention is a pressurised aerosol formulation, which is in the form of a mixture, to be sprayed as a cosmetic, room or medicinal spray, of a propellant gas and organic solvents, as the propellant, and also active compounds and solvents for the active compounds, wherein the improvement comprises that the mixture is in the form of a homogeneous solution and this contains at least 50 percent by weight, preferably at least 55 percent by weight, of non-combustible constituents—relative to the total weight of the mixture—and contains, as the propellant gases, carbon dioxide and dimethyl ether, and, as non-combustible constituents, at least water, carbon dioxide, methylene chloride and/or 1,1,1-trichloroethane. This pressurized aerosol formulation is during transport, on storage and in use a product of low accident risk for the indicated purpose.

18 Claims, No Drawings

PRESSURIZED AEROSOL FORMULATION AND PROCESS FOR THE MANUFACTURE THEREOF

BACKGROUND OF THE INVENTION

1. Field of the Invention

The present invention relates to a pressurised aerosol preparation of a self-propellant spray system, for use in cosmetics, for room treatment and/or in medicine, which is based on the active compounds to be administered, organic solvents and propellants in a spray container, preferably an aerosol can with an extremely fine atomiser valve.

2. Description of the Prior Art

Numerous self-propellant spray systems are already known. Thus, in U.S. Pat. No. 3,387,425, a process for the production of aerosol packs is described in which the agent to be administered is filled in the form of a liquid concentrate into a spray can, the spray can is then sealed with a valve and a saturated solution of a compressed gas, which consists of the group comprising carbon dioxide, nitrogen oxide and nitrogen in a normally gaseous liquefied chlorofluorinated saturated aliphatic hydrocarbon is filled, as the propellant, through the valve seal. Chlorofluorinated saturated aliphatic hydrocarbons, which are used in this process as dichlorodifluoromethane, trichloromonofluoromethane, dichlorotetrafluoroethane and mixtures thereof. For reasons of environmental protection, efforts are being made to prohibit the use of chlorofluorinated hydrocarbons of this type.

In German Auslegeschrift No. 2,327,067 (U.S. Pat. No. 3,996,153), a mixture of carbon dioxide and solvents, as the propellant, active compounds and solvents for the active compounds, which is to be sprayed from pressurised gas containers as a hair spray, body spray or room spray, is described, which is characterised in that the mixture contains, as the propellant, acetone and/or diethyl carbonate, into which 1 to 15% of carbon dioxide has been introduced under pressure up to saturation pressure of 6 atmospheres gauge. This spray has a high content of combustible constituents. In German Offenlegungsschrift No. 2,705,872, an aerosol is described which contains a liquid mixture of a hydrocarbon propellant, water and an organic solvent, characterised in that the liquid mixture forms a single phase and essentially consists of (a) 5 to 30 percent by weight of a hydrocarbon propellant, which supplies a pressure of 1.5 to 8.5 kp/cm$^2$ at 25° C. in the aerosol container, (b) 5 to 30 percent by weight of water, (c) 10 to 40 percent by weight of methylene chloride and/or 1,1,1-trichloroethane and (d) at least 37 percent by weight of ethanol, n-propanol and/or iso-propanol.

According to the data given on page 5 of this Offenlegungsschrift, at least 95 percent by weight of the liquid mixture must be formed from the said constituents (a) to (d), although smaller amounts of other organic liquids can be present, provided that they do not have a considerable adverse influence on the properties of the agent. Dimethoxymethane, ethyl acetate, acetone, dimethyl ether, diethyl ether, 2-methoxyethanol, 2-ethoxyethanol or a butanol are mentioned as examples. In addition to the hydrocarbon propellant, the aerosol can contain compressed gases, such as, for example, carbon dioxide and/or nitrous oxide. This known aerosol, which contains 5 to 30, and preferably 10 to 20, percent by weight of a hydrocarbon propellant in order to achieve a pressure of 1.5 to 8.5 kp/cm$^2$ at 25° C. in the aerosol container, has, however, the disadvantage that, as repetition of the work by the applicant has shown, single-phase aerosols containing at least 55 percent by weight of non-combustible constituents can never be obtained when this aerosol is prepared from the components a, b, c and d, which are chosen so that the conditions indicated in Patent Claims 1 to 4 are met. It is also not possible to obtain a single-phase aerosol of this type when the smaller amounts of other organic solvents and/or compressed gases, which are mentioned on page 5 of this Offenlegungsschrift are also used. The aerosol formulation according to the invention, however, does not contain any hydrocarbon propellant. The sudden advance achieved as a result of this can be seen from the comparison data given after the examples.

BRIEF SUMMARY OF THE INVENTION

The object of the present invention is to provide a mixture, which is to be sprayed from pressurised gas containers as a cosmetic, medicinal or room spray, of propellant gases and solvents, as the propellants, and also active compounds and solvents for the active compounds, which mixture 1. is in the form of a stable, homogeneous solution—that is to say as a single phase—in the pressurised gas container, so that it is always dispensed in the same composition when the spray is used, 2. has as high as possible a proportion of non-combustible constituents in the solution, so that transport, storage and use can take place as far as possible without risk of accidents and without pollution of the environment, and 3. is free from chlorofluorinated hydrocarbons and hydrocarbon propellant gases and thus is a safe aerosol formulation.

The invention relates to a pressurised aerosol formulation, which is in the form of a mixture, to be sprayed as a cosmetic, room or medicinal spray, of a propellant gas and organic solvents, as the propellant, and also active compounds and solvents for the active compounds, characterised in that the mixture is in the form of a homogeneous solution and this contains at least 50 percent by weight, preferably at least 55 percent by weight, of non-combustible constituents—relative to the total weight of the mixture—and contains, as the propellant gases, carbon dioxide and dimethyl ether, and, as non-combustible constituents, at least water, carbon dioxide, methylene chloride and/or 1,1,1-trichloroethane, and a process for its manufacture and its use as a product having a low accident risk.

Solvents which can be used as organic solvents for the propellant gases, in order to form the propellant, and as solvents for the active compounds are acetone, ethyl methyl ketone, diethyl ether, dimethoxymethane, diethyl carbonate, ethyl alcohol, n-propanol, iso-propanol, methyl acetate, ethyl acetate, methoxyacetone, hydroxyacetone, methyl isopropyl ketone, diethyl ketone, diisopropyl ketone, dipropyl ketone, diacetone alcohol, dichloroethylene, ethyl chloride, 1,1-dichloroethane and 1-chlorobutane, individually or as mixture.

In the sense of this invention, non-combustible constituents are understood as water, carbon dioxide, methylene chloride and/or 1,1,1-trichloroethane and those further constituents, for example active compounds, which have an ignition temperature above 600° C.

The formulations according to the invention can be formulated with cosmetic, hygienically or medicinally active constituents (active compounds) and give formulations for different purposes, for example as a cosmetic, room or medicinal spray.

Active constituents which can be contained in the formulations are, for example, hair care substances, hair spray resin, antiperspirants, deodorants, bactericidal agents, perfume, fungicides, vegetable extracts and/or organ extracts.

The propellant system used in the formulations according to the invention is based on the propellant gases carbon dioxide and dimethyl ether and organic solvents as the propellant. The propellant system contains, as materials soluble in the propellant, methylene chloride and/or 1,1,1-trichloroethane and also water.

One embodiment of the aerosol formulation is characterised in that it contains, as propellant gases, 4 to 6 percent by weight of carbon dioxide and 6 to 10 percent by weight of dimethyl ether, the percentages by weight being based on the total weight of the constituents filled into the container.

Another embodiment of the aerosol formulation is characterised in that it contains 12.9 to 18 percent by weight of water, the percentages by weight being based on the total weight of the constituents filled into the container.

A further embodiment of the aerosol formulation is characterised in that it contains 32 to 35 percent by weight of methylene chloride and/or 1,1,1-trichloroethane, the percentages by weight being based on the total weight of the constituents filled into the container.

A further embodiment of the aerosol formulation is characterised in that it contains 33 to 43 percent by weight of organic solvents for propellant gases and active compounds, the percentages by weight being based on the total weight of the constituents filled into the container.

DETAILED DESCRIPTION OF THE PREFERRED EMBODIMENTS OF THE INVENTION

In a preferred embodiment, the aerosol formulation is characterised in that it contains 12.9 to 17.5 percent by weight of water, 4 to 6 percent by weight of carbon dioxide, 6 to 8 percent by weight of dimethyl ether, 35 to 40 percent by weight of organic solvents, 32 to 35 percent by weight of methylene chloride and/or 1,1,1-trichloroethane and 0.5 to 3.1 percent by weight of active compound, the indicated percentages by weight having to add up to 100 percent by weight.

The nature and amount of the required active compound, organic solvent for the propellant gases, solvent for the active compounds, carbon dioxide, dimethyl ether, water and also methylene chloride and/or 1,1,1-trichloroethane are so matched qualitatively and quantitatively in a sample batch, taking into account the intended use and taking into account the ranges given above for the percentages by weight, that a homogeneous solution forms as a single phase which can be sprayed flawlessly as a ready-to-use aerosol.

DETAILED DESCRIPTION OF THE MOST PREFERRED EMBODIMENTS OF THE INVENTION

Taking into account the above rules for technical handling, the following tolerance range was determined for a specific aerosol formulation according to the invention, which was in the form of a homogeneous solution and a single phase and could be sprayed flawlessly: 13.62 to 14.35 percent by weight of water, 4.57 to 4.27 percent by weight of carbon dioxide, 6.95 to 7.76 percent by weight of dimethyl ether, 34.06 to 32.86 percent by weight of iso-propanol and/or ethanol and/or n-propanol, 3.72 to 4 6 percent by weight of acetone and/or methoxyacetone, 35.0 to 33.93 percent by weight of methylene chloride and/or 1,1,1-trichloroethane and 2.08 to 2.47 percent by weight of active compounds.

In this case also the data for the percentages by weight are to be so chosen that their sum adds up to 100 percent by weight. In manufactured aerosol formulations of the above most preferred embodiment, the content of non-combustible constituents was 55.02 to 55.33 percent by weight. Compared with the state of the art according to German Offenlegungsschrift No. 2,705,872, Example 2, with a maximum of 40 percent by weight of non-combustible constituents, this typifies a sudden advance. For this reason, the aerosol formulations of the invention are used as a product of low accident risk for the indicated purpose, during transport, on storage and in use, so that it can be designated a "safe aerosol formulation".

The most preferred embodiment which has been illustrated above, of the pressurised aerosol formulation is illustrated by Examples 1 to 16.

A process for the manufacture of a usable aerosol formulation is characterised in that the active compounds, water, organic solvents for the propellant gases and solvents for the active compounds, and also methylene chloride and/or 1,1,1-trichloroethane, are so processed to a mixture, and a requisite partial amount is filled into a pressurised spray container and the pressurised spray container is then sealed, that, after dimethyl ether and then carbon dioxide have been filled into the container under pressure, the liquid packing is in the form of a single-phase homogeneous solution under a pressure of about 5 to 7 bars after filling. The invention is illustrated by the following examples:

EXAMPLE 1

(Hair spray—aerosol formulation)

The following constituents were used:
Copolymer of N-vinylpyrrolidone and vinyl acetate in a ratio of 30:70 (hair spray resin): 2.37 g
Water: 13.70 g
Methylene chloride: 34.69 g
Iso-propanol: 33.65 g
Acetone: 3.97 g
Dimethyl ether: 6.95 g
Carbon dioxide: 4.57 g
Perfume oil (active compound): 0.10 g The hair spray resin was dissolved in the mixture of methylene chloride, iso-propanol and acetone, perfume oil was added and water was added whilst stirring. The batch was filled into an aerosol container. The container was sealed with an extremely fine atomiser valve and dimethyl ether was introduced under pressure through the valve. The indicated amount of carbon dioxide was then passed in.

EXAMPLE 2

(Hair spray—aerosol formulation)

The following constituents were used:
Copolymer of N-vinylpyrrolidone and vinyl acetate in a ratio of 30:70 (hair spray resin): 2.47 g
Water: 14.35 g
Methylene chloride: 33.93 g
Ethyl alcohol: 32.86 g Methoxyacetone: 4.26 g
Dimethyl ether: 7.76 g
Carbon dioxide: 4.27 g
Perfume oil (active compound): 0.10 g The hair spray resin was dissolved in the mixture of methylene chloride, ethyl alcohol and methoxyacetone, perfume oil was added and water was added whilst stirring well. The batch was filled into an aerosol container. The container was sealed with an extremely fine atomiser valve and dimethyl ether was introduced under pressure through the valve. The indicated amount of carbon dioxide was then passed in.

EXAMPLE 3

(Hair spray—aerosol formulation)

The following constituents were used:
Copolymer of N-vinylpyrrolidone and vinyl acetate in a ratio of 30:70 (hair spray resin): 2.08 g
Water: 13.62 g
1,1,1-Trichloroethane: 35.00 g
Iso-propanol: 33.96 g
Acetone: 3.72 g
Dimethyl ether: 6.95 g
Carbon dioxide: 4.57 g
Perfume oil (active compound): 0.10 g The hair spray resin was dissolved in the mixture of methylene chloride, iso-propanol and acetone, perfume oil was added and water was added whilst stirring well. The batch was filled into an aerosol container. The container was sealed with an extremely fine atomiser valve and dimethyl ether was introduced under pressure through the valve. The indicated amount of carbon dioxide was then passed in.

EXAMPLE 4

(Deodorant spray—aerosol formulation)

The following constituents were used:
2,4,4'-Trichloro-2'-hydroxydiphenyl ether (active compound): 0.10 g
Ethyl benzoate (active compound): 2.37 g
Water: 14.35 g
1,1,1-Trichloroethane: 33.93 g
Iso-propanol: 32.86 g
Acetone: 3.86 g
Dimethyl ether: 7.76 g
Carbon dioxide: 4.27 g
Perfume oil (active compound): 0.50 g The active compounds were dissolved in the mixture of acetone, iso-propanol, 1,1,1-trichloroethane and water. The batch was filled into an aerosol container. The container was sealed with an extremely fine atomiser valve and dimethyl ether was introduced under pressure through the valve. The indicated amount of carbon dioxide was then passed in.

EXAMPLE 5

(Deodorant spray—aerosol formulation)

The following constituents were used:
2,4,4'-Trichloro-2'-hydroxydiphenyl ether (active compound): 0.10 g
Ethyl benzoate (active compound): 1.98 g
Water: 13.62 g
1,1,1-Trichloroethane: 35.00 g
Ethanol: 33.56 g
Methoxyacetone: 3.72 g
Dimethyl ether: 6.95 g
Carbon dioxide: 4.57 g
Perfume oil (active compound): 0.50 g The active compounds were dissolved in the mixture of methoxyacetone, ethyl alcohol, 1,1,1-trichloroethane and water. The batch was filled into an aerosol container. The container was sealed with an extremely fine atomiser valve and dimethyl ether was introduced under pressure through the valve. The indicated amount of carbon dioxide was then passed in.

EXAMPLE 6

(Room spray—aerosol formulation)

The following constituents were used:
Ethyl benzoate (active compound): 2.08 g
Water: 13.62 g
1,1,1-Trichloroethane: 35.00 g
Iso-propanol: 33.06 g
Methoxyacetone: 3.72 g
Dimethyl ether: 6.95 g
Carbon dioxide: 4.57 g
Perfume oil (active compound): 1.00 g The active compound and the perfume oil were dissolved in the mixture of 1,1,1-trichloroethane, iso-propanol, methoxyacetone and water. The batch was filled into an aerosol container. The container was sealed with an extremely fine atomiser valve and dimethyl ether was introduced under pressure through the valve. The indicated amount of carbon dioxide was then passed in.

EXAMPLE 7

(Hair spray-aerosol formulation)

By the similar procedure as described in example 1 the aerosol formulation was produced but the following constituents were used:
Copolymer of N-vinylpyrrolidone and vinylacetate in a ratio of 30:70 (hair spray resin): 2.37 g
Methylene chloride: 34.69 g
Iso-propanol: 11.00 g
Ethanol: 11.00 g
n-Propanol: 11.65 g
Acetone: 3.97 g
Dimethyl ether: 6.95 g
Carbon dioxide: 4.57 g
Perfume oil: 0.10 g
Water: 13.70 g

EXAMPLE 8

(Deodorant spray-aerosol formulation)

By the similar procedure as described in example 4 the aerosol formulation was produced but 1,1,1-trichloroethane was substituted by 33.93 g methylene chloride. Further ethyl benzoate was substituted by the same amount of diacetone alcohol.

EXAMPLE 9

(Deodorant spray-aerosol formulation)

By the similar procedure as described in example 4 the aerosol formulation was produced but iso-propanol was substituted by 32.86 ethanol.

EXAMPLE 10

(Deodorant spray-aerosol formulation)

By the similar procedure as described in example 4 the aerosol formulation was produced but 1,1,1-trichloroethane was substituted by a mixture consisting of 3.393 g 1,1,1-trichloroethane and 30.537 g methylene-chloride.

EXAMPLE 11

(Deodorant spray-aerosol formulation)

By the similar procedure as described in example 4 the aerosol formulation was produced but 1,1,1-trichloroethane was substituted by a mixture consisting of 16.965 g methylene chloride and 16.965 g 1,1,1-trichloroethane. Further iso-propanol was substituted by a mixture consisting of 16.43 ethanol and 16.43 iso-propanol.

EXAMPLE 12

(Deodorant spray-aerosol formulation)

By the similar procedure as described in example 5 the aerosol formulation was produced but 1,1,1-trichloroethane was substituted by 35.00 g methylene chloride. Further ethyl benzoate was substituted by the same amount of diacetone alcohol.

EXAMPLE 13

(Deodorant spray-aerosol formulation)

By the similar procedure as described in example 5 the aerosol formulation was produced, but ethanol was substituted by 33.56 g iso-propanol.

EXAMPLE 14

(Deodorant spray-aerosol formulation)

By the similar procedure as described in example 5 the aerosol formulation was produced but 1,1,1-trichloroethane was substituted by a mixture consisting of 17.5 g methylene chloride and 17.5 g 1,1,1-trichloroethane. Further, ethanol was substituted by a mixture consisting of 16.78 g iso-propanol and 16.78 g ethanol.

EXAMPLE 15

(Hair spray-aerosol formulation)

By the similar procedure as described in example 1 the aerosol formulation was produced, but acetone was substituted by 3.97 g ethyl acetate, and further, methylene chloride was substituted by 34.69 g 1,1,1-trichloroethane.

EXAMPLE 16

(Room spray-aerosol formulation)

By the similar procedure as described in example 6 the aerosol formulation was produced but iso-propanol was substituted by a mixture consisting of 16.53 g ethanol and 16.53 g n-propanol.

All of the aerosol formulations which have been described in examples 1 to 16 are in the form of a homogeneous solution and in the form of a single phase in container. All of the aerosol formulations according to examples 1 to 16 were readily sprayable at 20° C., so that the total contents of the can were used as intended. The ready to use aerosol products according to examples 1 to 16 are under a pressure of about 5 to 7 bars after filling.

Further experiments with quota samples have shown, that in the aerosol formulation of the invention with about the formulation 13.62 to 14.35 percent by weight of water
4.57 to 4.27 percent by weight of carbon dioxide
6.95 to 7.76 percent by weight of dimethyl ether
37.78 to 37.22 percent by weight of organic solvents
35.00 to 33.93 percent by weight of methylene chloride and/or 1,1,1-trichloroethane and
2.08 to 2.47 percent by weight of active compounds, the percentages by weight having to add up to 100 percent by weight, with consideration of the purpose of use at the time of examination of drawn samples, characterised in that the mixtures are in the form of a homogeneous solution, forms as a single phase which can be sprayed flawlessly as a ready-to-use aerosol. In these drawn samples the following organic solvents could be co-used alone in the following amounts:

Acetone 3.72–4.36 percent by weight,
Ethylacetate up to 4.36 percent by weight in combination with 1,1,1-trichloroethane only,
Diacetone alcohol 1.98–2.37 percent by weight,
Dimethoxymethane up to 4.36 percent by weight in combination with 1,1,1-trichloroethane,
Hydroxyacetone 3.72–4.36 percent by weight,
Methoxyacetone 3.72–4.36 percent by weight,
Methyl acetate up to 4.36 percent by weight, in combination with 1,1,1-trichloroethane only,
Ethyl methyl ketone up to 4.36 percent by weight in combination with 1,1,1-trichloroethane only,
Methyl isopropyl ketone up to 4.36 percent by weight in combination with 1,1,1-trichloroethane.

Further drawn samples have shown that mixtures consisting of hydroxyacetone and methoxyacetone can be used in the range of 3.72 to 4.36 percent by weight.

| Comparison data for the non-combustible constituents in an aerosol formulation to demonstrate the technical advance achieved with regard to German Offenlegungsschrift 2,705,872 | | | | | | | | | | |
|---|---|---|---|---|---|---|---|---|---|---|
| Example No. | 1 | 2 | 3 | 4 | 5 | 6 | 7 | 8 | 9 | 10 |
| State of the art German Offenlegungsschrift 2,705,872, non-combustible constituents in percent by weight | 37 | 40 | 38 | 36 | 31 | 25 | 18 | 35.2 | 35.2 | 25 |
| Aerosol formulation of the invention, non-combustible constituents in percent by weight | 55.33 | 55.02 | 55.27 | 55.02 | 55.27 | 55.28 | 55.33 | 55.02 | 55.02 | 55,02 |

When calculating the comparison data for the non-combustible constituents, the following components were taken into account: hair spray resin, methylene chloride, water, carbon dioxide, 2,4,4′-trichloro-2′-hydroxydiphenyl ether, 1,1,1-trichloroethane and ethyl benzoate.

The basic aluminium chloride/propylene glycol complex contained in Example 10 of German Offenlegungsschrift No. 2,705,872 was assumed to be 50 percent by weight non combustible.

The above comparison data show that a markedly improved aerosol formulation is provided by the present invention, since, according to the state of the art, in the most advantageous case the content of non-combustible constituents in the aerosol formulation free from fluorinated hydrocarbons is 40 percent by weight, whilst in the case of the aerosol formulation of the invention the content of non-combustible constituents is at least 55.02 percent by weight in all examples.

What we claim is:

1. A pressurized aerosol formulation, which is in the form of a mixture, to be sprayed as a cosmetic, room or medicinal spray, of a propellant gas and organic solvents for the propellant gas, as the propellant, and also active compounds and solvents for the active compounds, wherein the mixture is in the form of a homogeneous solution and the solution contains at least 50 percent by weight of non-combustible constituents relative to the total weight of the mixture and contains, as propellant gases, carbon dioxide and dimethyl ether, and, as non-combustible constituents, at least water, carbon dioxide, methylene chloride, 1,1,1-trichloroethane, or a mixture of methylene chloride and 1,1,1-trichloroethane, wherein said organic solvents are selected from the group consisting of acetone, ethyl methyl ketone, diethyl ether, dimethoxymethane, diethyl carbonate, ethyl alcohol, n-propanol, isopropanol, methyl acetate, ethyl acetate, methoxyacetone, hydroxyacetone, methyl isopropyl ketone, diethyl ketone, diisopropyl ketone, dipropyl ketone, dichloroethylene, ethyl chloride, 1,1-dichloroethane, 1-chlorobutane, and mixtures thereof.

2. An aerosol formulation according to claim 1, characterised in that it contains, as propellant gases, 4 to 6 percent by weight of carbon dioxide and 6 to 10 percent by weight of dimethyl ether, the percentages by weight being based on the total weight of the constituents filled into a container.

3. An aerosol formulation according to claim 2, characterised in that it contains 12.9 to 18 percent by weight of water, the percentages by weight being based on the total weight of the constituents filled into the container.

4. An aerosol formulation according to claim 3, characterised in that it contains 32 to 35 percent by weight of methylene chloride and/or 1,1,1-trichloroethane, the percentages by weight being based on the total weight of the constituents filled into the container.

5. An aerosol formulation according to claim 4, characterised in that it contains 33 to 43 percent by weight of organic solvents for propellant gases and active compounds, the percentages by weight being based on the total weight of the constituents filled into the container under a pressure of about 5 to 7 bars after filling.

6. An aerosol formulation according to claim 1, characterised in that it contains 12.9 to 17.5 percent by weight of water, 4 to 6 percent by weight of carbon dioxide, 6 to 8 percent by weight of dimethyl ether, 35 to 40 percent by weight of organic solvents, 32 to 35 percent by weight of methylene chloride and/or 1,1,1-trichloroethane and 0.5 to 3.1 percent by weight of active compounds, the percentages by weight being based on the total weight of the constituents filled into a container and there having to add up to 100 percent by weight.

7. An aerosol formulation according to claim 1, characterised in that it contains 13.62 to 14.35 percent by weight of water, 4.57 to 4.27 percent by weight of carbon dioxide, 6.95 to 7.76 percent by weight of dimethyl ether, 34.06 to 32.86 percent by weight of iso-propanol and/or ethanol and/or n-propanol, 3.72 to 4.26 percent by weight of acetone and/or methoxyacetone, 35.00 to 33.93 percent by weight of methylene chloride and/or 1,1,1-trichloroethane and 2.08 to 3.09 percent by weight of active compounds, the percentages by weight having to be based on the total weight of the constituents filled into a container.

8. A sprayable, pressurized, aerosol formulation for use as a cosmetic, room or medicinal spray, said formulation comprising a homogeneous solution of
at least one active compound and at least one solvent for said active compound;
a propellant consisting essentially of a propellant gas and at least one organic solvent for said propellant gas, wherein said propellant gas comprises a mixture of carbon dioxide and dimethyl ether; and
at least 50 percent by weight, based on total weight of said homogeneous solution, of non-combustible constituents consisting essentially of water, carbon dioxide and a member selected from the group consisting of methylene chloride, 1,1,1-trichloroethane and a mixture of methylene chloride and 1,1,1-trichloroethane;
wherein said formulation is substantially free from chlorofluorinated hydrocarbon or hydrocarbon propellant gases, and wherein said solvent for said active compound and said solvent for said propellant gas are selected from the group consisting of acetone, ethyl methyl ketone, diethyl ether, dimethoxymethane, diethyl carbonate, ethyl alcohol, n-propanol, isopropanol, methyl acetate, ethyl acetate, methoxyacetone, hydroxyacetone, methyl isopropyl ketone, diethyl ketone, diisopropyl ketone, dipropyl ketone, dichloroethylene, ethyl chloride, 1,1-dichloroethane 1-chlorobutane, and mixtures thereof.

9. An aerosol formulation according to claim 8, wherein said propellant gas comprises about 4 to about 6 percent by weight carbon dioxide and about 6 to about 10 percent by weight dimethyl ether, and said non-combustible constituents include 12.9 to about 18 percent by weight water, and said formulation contains about 33 to about 43 percent by weight of organic solvents for propellant gases and active compounds.

10. An aerosol formulation according to claim 8 or 9, wherein said formulation is substantially free from fluorinated hydrocarbons.

11. An aerosol formulation according to claim 8 or 9, wherein said non-combustible constituents include 1,1,1-trichloroethane or a mixture of 1,1,1-trichloroethane and methylene chloride.

12. A process for the manufacture of the pressurized aerosol formulation according to claim 1, characterized in that organic solvents for the propellant gases, in order to form the propellant and also as solvents for the active compounds, and, as non-combustible constituents, at least water, methylene chloride and/or trichloroethane are filled into a pressurized container and, after a spray valve has been fitted, dimethyl ether and then carbon dioxide are passed in, the nature and amount of the constituents being qualitatively and quantitatively so matched, taking into account the intended use, that the pressurized packing contains at least 55 percent by weight of non-combustible constituents and the liquid phase is in the form of a homogeneous solution under a pressure of about 5 to 7 bars after filling.

13. A process according to claim 12, characterised in that 4 to 6 percent by weight of carbon dioxide and 6 to 10 percent by weight of dimethyl ether are filled into a container as propellant gases, the percentages by weight being based on the total weight of the packing.

14. A process according to claim 13, characterised in that water is filled into the container in amounts of 12.9 to 18 percent by weight, the percentages by weight being based on the total weight of the packing.

15. A process according to claim 14, characterised in that 32 to 35 percent by weight of methylene chloride and/or 1,1,1-trichloroethane are filled into the container, the percentages by weight being based on the total weight of the packing.

16. A process according to claim 15, characterised in that 33 to 45 percent by weight of organic solvents for propellant gases and active compounds are filled into the container, the percentages by weight being based on the total weight of the packing.

17. A process according to claim 12, characterised in that the constituents are filled into a container in amounts of 12.9 to 17.5 percent by weight of water, 4 to 6 percent by weight of carbon dioxide, 6 to 8 percent by weight of dimethyl ether, 35 to 40 percent by weight of organic solvents, 32 to 35 percent by weight of methylene chloride and/or 1,1,1-trichloroethane and 0.5 to 3.1 percent by weight of active compounds, the percentages by weight being based on the total weight of the packing.

18. A process according to claim 12, characterised in that the constituents are filled into a container in amounts of 13.62 to 14.35 percent by weight of water, 4.57 to 4.27 percent by weight of carbon dioxide, 6.95 to 7.76 percent by weight of dimethyl ether, 34.06 to 32.86 percent by weight of iso-propanol and/or ethanol and/or n-propanol, 3.72 to 4.36 percent by weight of acetone and/or methoxyacetone, 35.00 to 33.93 percent by weight of methylene chloride and/or 1,1,1-trichloroethane and 2.08 to 2.47 percent by weight of active compounds, the percentages by weight being based on the total weight of the packing.

* * * * *